United States Patent [19]

Powell et al.

[11] Patent Number: 4,532,327
[45] Date of Patent: Jul. 30, 1985

[54] SESBANIMIDE AND THE USE THEREOF IN TREATING LEUKEMIC TUMORS

[75] Inventors: Richard G. Powell, Peoria; Cecil R. Smith, Jr., Dunlap, both of Ill.

[73] Assignee: The United States of America as represented by the Secretary of Agriculture, Washington, D.C.

[21] Appl. No.: 566,469

[22] Filed: Dec. 28, 1983

[51] Int. Cl.³ .......................................... C07D 405/00
[52] U.S. Cl. .................................................... 546/214
[58] Field of Search ................ 546/207, 214; 424/267

[56] References Cited

U.S. PATENT DOCUMENTS

| | | | |
|---|---|---|---|
| 3,882,124 | 5/1975 | Kirchlechner et al. | 546/207 |
| 4,200,639 | 4/1980 | Powell | 424/256 |
| 4,279,902 | 7/1981 | Hauck et al. | 546/207 |

OTHER PUBLICATIONS

Kinoshita et al., Abstract No. 75, 185th ACS National Meeting, Mar. 20–25, 1983.
R. G. Powell et al., "Antitumor Activity of *Sesbania vesicaria, S. punicea,* and *S. drummondii* Seed Extracts," Planta Med. 30(1): 1–8, (Aug. 1976).
R. G. Powell et al., "An Investigation of the Antitumor Activity of *Sesbania drummondii*," J. Nat. Prod. 44(1): 86–90, (Jan.–Feb. 1981).
"Sesbanimide–A New Antitumor Compound," Northern Regional Research Center (NRRC) Notes from the Director, Issue #1531, (Jan. 14, 1983).
R. G. Powell et al., "Sesbanimide, A Potent Antitumor Substance from *Sesbania drummondii* Seed," Abstract #74, Abstracts of Papers, 185th ACS National Meeting, Seattle, WA., Mar. 20–25, 1983.
R. G. Powell et al., "Sesbanimide, A Potent Antitumor Substance from *Sesbania drummondii* Seed," J. Amer. Chem. Soc. 105(11): 3739–3741, (1983).
R. G. Powell et al., "Sesbanimide," Proceedings of Symposium on Discovery and Development of Naturally Occurring Antitumor Agents, Frederick, MD., Jun. 27–29, 1983.

*Primary Examiner*—Ethel G. Love
*Attorney, Agent, or Firm*—M. Howard Silverstein; David G. McConnell; Curtis P. Ribando

[57] ABSTRACT

A novel alkaloid compound named "sesbanimide" has been isolated from the tissue of a leguminous plant known as *Sesbania drummondii.* Sesbanimide is characterized by the structural formula

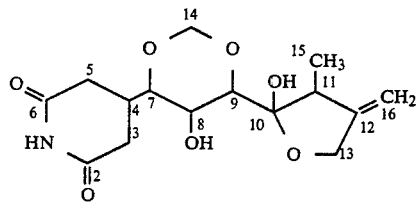

and is effective as an antineoplastic agent in animals.

5 Claims, No Drawings

SESBANIMIDE AND THE USE THEREOF IN TREATING LEUKEMIC TUMORS

BACKGROUND OF THE INVENTION

1. Field of the Invention

This invention relates to a novel alkaloid compound which is useful as a chemotherapeutic agent for the remission of leukemia in animals.

2. Description of the Prior Art

A number of leguminous plants belonging to the genus *Sesbania* are notorious for the toxicity of their seeds. These species, including *S. vesicaria, S. punicea,* and *S. drummondii,* having been linked to the poisoning of the livestock and poultry in the Southern Coastal Plain of the United States [J. M. Kingsbury, Poisonous Plants of the United States and Canada (1964), pp. 353–357]. Seeds of *S. drummondii,* also known as coffeebean, rattlebrush, and rattlebox, are reportedly characterized by a minimum lethal amount for sheep of about 0.1% of the animal's weight. Efforts to identify the toxic principle of these species have led to isolation of a variety of saponins and sapogenins, none of which has been documented as being toxic. A sapotoxin isolated from *S. drummondii* (*Daubentonia longifolia*) has been claimed as a contributing factor [A. Robey, "Isolation of the Toxin of *Daubentonia longifolia,*" Thesis, Texas A&M Coll. (1925)].

In a search for chemical compounds which are chemotherapeutically active against leukemia systems, the three toxic species of *Sesbania* named above were screened by Powell et al. [Planta Med. 30(1): 1–8 (August 1976)]. For each plant, an ethanolic seed extract tested positive against lymphocytic leukemia P388 (PS) in mice. Certain enriched fractions were obtained from the seed extract of *S. vesicaria,* but the responsible agent or agents were not successfully isolated, identified, or obtained in a therapeutically acceptable form.

Powell, U.S. Pat. No. 4,200,639, now disclaimed, succeeded in isolating the tricyclic compound sesbanine from *S. drummondii.* Apparent activity in the KB cell screen and in the PS tumor system attributed to sesbanine in the patent disclosure was subsequently established to be the result of a heretofore unidentified impurity in the assayed fractions.

SUMMARY OF THE INVENTION

In an effort to identify the compound responsible for the activity of *Sesbania drummondii* seed tissue fractions against leukemia in animals, we have now discovered a novel alkaloid compound which demonstrates potent activity in leukemia test systems. This compound has been given the name sesbanimide and has been isolated in a pure crystalline and therapeutically acceptable form, free of interfering toxic agents. It incorporates a previously unreported tricyclic structure consisting of three rings linked by single bonds and is characterized by the following formula:

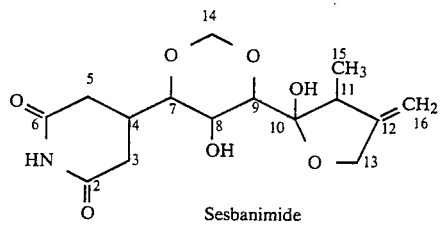

The IUPAC name is 2,6-Piperidinedione, 4-[5-hydroxy-6-(tetrahydro-2-hydroxy-3-methyl-4-methylene-2-furanyl)-1,3-dioxan-4-yl]-.

In accordance with this discovery, it is an object of the invention to introduce sesbanimide as a novel chemical compound having antineoplastic activity.

Another object of this invention is to isolate sesbanimide in substantially pure form from *S. drummondii* seed material.

It is also an object of the invention to administer the novel alkaloid compound to animals in order to cause remission of leukemia therein.

Other objects and advantages of the invention will become readily apparent from the ensuing description.

DETAILED DESCRIPTION OF THE INVENTION

As mentioned above, the starting material for use in this invention is the seed of *S. drummondii.* This plant species has also been classified under the synonomous names *Daubentonia longifolia* DC and *Daubentonia drummondii* as described in further detail by Kingsbury, supra.

The seed material is prepared for extraction by grinding it in a conventional mill to a suitable particle size in the range of about 0.1–5 mm. in diameter, and generally in the range of 0.5–2 mm. The ground material is then extracted with a polar solvent such as an alcohol, preferably methanol or 95% ethanol. The solvent extract is separated from the solid residue and is connected to a thin syrup. After dilution with water, the syrup is partitioned with an immiscible solvent, which is capable of removing the pigments and lipids. Petroleum ether, hexane, and other nonpolar solvents are suitable for this purpose. Active materials are removed from the lipid-free aqueous alcohol fraction by partitioning with an appropriate solvent such as butanol or dichloromethane. The recovered solvent phase constitutes the crude alkaloid extract.

Separation and purification of sesbanimide from the crude extract can be effected by the use of the proper combination of conventional techniques including, for example, countercurrent distribution (CCD), column chromatography (CC), high-performance liquid chromatography (HPLC), and thin-layer chromatography (TLC). In the preferred embodiment of the invention, we have successfully employed a sequence of operations comprising CC on silica and HPLC on silica with recrystallization from dichloromethane as necessary. While not desiring to be limited thereto, the details of the separation procedure are illustrated by the following examples. Fractionation was guided by assay against KB cell culture and PS leukemia in mice.

EXAMPLE 1

Isolation of Sesbanimide. *S. drummondii* seed material (454 kg.) was ground in a Fitz mill to a particle size of 0.5–2.0 mm. in diameter immediately prior to extraction. The ground material was placed in a 2270-l. tank containing 908 l. of 95% ethanol, heated to 50°, and stirred overnight. The ethanol extract was removed and the seed material was similarly extracted four more times, each with 450 l. of 95% ethanol. Ethanol extracts were combined and concentrated in a vacuum evaporator to a light syrup estimated to contain 25 kg. of alcohol solubles. The concentrate was diluted with sufficient water to give 227 l. of an ethanol-water (1:3) solution, which was defatted by partitioning three times with a total of 400 l. of petroleum ether. Petroleum ether solubles amounted to 10.1 kg. Alcohol was then removed from the aqueous layer by concentrating to a volume of 45 l.; an equal volume of water was added, and the resulting solution was extracted once with 90 l. of 1-butanol and twice with 45 l. of 1-butanol. Butanol solubles were concentrated in an evaporator yielding 6.7 kg. of a thick syrup.

Butanol soluble material, 6.6 kg., was then passed through a 10-carboy CCD in four batches. Each carboy contained 16 l. of a three-component biphasic solvent: water, ethyl acetate, and methanol in a 2:2:1 ratio, adjusted to equal phase volumes. Based on activity, fraction 3 (F080), 675 g., was selected for further workup. The fraction was divided into nine equal portions, and each portion was chromatographed on activity grade III neutral alumina using 3 l. of $CH_2Cl_2$–MeOH (2:1) as the eluting solvent. Similar fractions from all nine column runs were combined on the basis of TLC similarity, yielding two fractions (F354 and F355) of activity-enriched material totaling 19 g. Further concentration was achieved by column chromatography of the combined fractions on columns packed with 150 g. of silica (two batches). Eluting solvents for both runs consisted of a step-wise gradient of methanol in dichloromethane: 750 ml. each of $CH_2Cl_2$, $CH_2Cl_2$—MeOH (95:5), $CH_2Cl_2$—MeOH (9:1), $Ch_2Cl_2$—MeOH (3:1), $CH_2Cl_2$—MeOH (1:1), and MeOH. Similar fractions were again combined on the basis of TLC analysis, and the most active fraction (F382), 1.6 g., was that which had been eluted with $CH_2Cl_2$—MeOH (95:5). Separation was continued with F382 by HPLC on silica, $CH_2Cl_2$—MeOH (97.5:2.5) and the activity of the second fraction (F387) was enriched by two successive preparative TLC separations on silica plates developed with $CH_2Cl_2$—MeOH (9:1). TLC fraction F402 was then subjected to HPLC on $C_{18}$ reversed phase $\mu$ Bondapak column using an $H_2O$—MeOH (4:1) solvent system at a flow rate of 2 ml./min. At 22 min., 4.5 mg. of substantially pure compound labeled sesbanimide B was eluted, and at 25 min., 17.1 mg. of substantially pure sesbanimide A was eluted.

Final purification of sesbanimide A by preparative TLC on silica gave a crystalline material (K443) having the following properties: $R_f$ 0.5; m.p. 158°–159° C.; IR ($CHCl_3$) 3555, 3480, 3380, 2945, 2880, 1700, 1080 cm.$^{-1}$; UV, end absorption <220 nm; $[\alpha]_D^{23}$ −5.6° (c 0.27, MeOH). Analysis calculated for $C_{15}H_{21}NO_7$: C, 55.06%; H, 6.42%; N, 4.28%. Analysis found: C, 54.94%; H, 6.42%; N, 4.22%.

The sesbanimide B was also purified by preparative TLC on silica, but attempts to crystallize it from mixtures of ethyl ether-dichloromethane yielded a colorless glass of substantially pure compound (K442) characterized by the following properties: $R_f$ 0.4; IR ($CHCl_3$) 3480, 3320, 2940, 2890, 1695, 1080 cm.$^{-1}$.

Characterization of Sesbanimide Isomers. Evidenced by repeated isolation procedures, the predominant stereochemical configuration of sesbanimide naturally occurring in *S. drummondii* is that corresponding to the isomer identified as sesbanimide A. The total absence of sesbanimide B in some isolation schemes suggests that it may be an inversion product of the 'A' form induced by one or more of the fractionation steps described in Example 1. The difference between sesbanimides A and B resides in the orientation of the methyl group on chiral carbon 11 as depicted below:

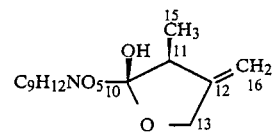

Sesbanimide A

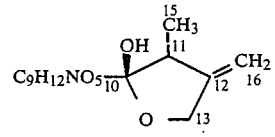

Sesbanimide B

While these are the only sterochemical isomers thus far identified, it is understood that others may exist by virtue of the other chiral carbons. Of course, all biologically active forms of the sesbanimide compound are considered to be within the scope of the invention.

Chemotherapeutic Activity. The chemotherapeutic activities of the fractions obtained in the isolation procedure of Example 1 were determined in part by a KB Cell Culture Screen in accordance with the National Cancer Institute Protocol 1.600 [Geran et al., Cancer Chemother, Rep., Part 3, 3(2): 17 (1972)]. The results of this procedure was expressed as the dose that inhibits growth to 50% of control growth by 3 days after drug addition. Such a dose is referred to as $ED_{50}$ and activity is indicated for $ED_{50}$ levels of $\leq 30$ $\mu$g./ml. The smaller than $ED_{50}$ level, the more active the test material. The KB activities of the fractions identified in Example 1 are reported below in Table I.

TABLE I

| KB Activities for Example 1 Fractions | |
|---|---|
| Fraction | $ED_{50}$ ($\mu$g./ml.) |
| F080 | $2.2 \times 10^0$ |
| F354 | $2.1 \times 10^0$ |
| F355 | $9.2 \times 10^{-1}$ |
| F382 | $5.1 \times 10^{-2}$ |
| F387 | $6.6 \times 10^{-2}$ |
| F402 | $<1.0 \times 10^{-1}$ |
| K442 | $6.8 \times 10^{-2}$ |
| K443 | $7.7 \times 10^{-3}$ |

As previously mentioned, the fractionation of Example 1 was also guided by assaying the effectiveness of the various fractions against lymphocytic leukemia cells of the strain P388 (PS tumors) implanted in mice. These assays were made according to the National Cancer Institute Protocol 1.200 described in Geran et al., supra, page 9. Starting 24 hr. after the tumor implantation, previously determined dosages of each fraction were injected intraperitoneally once a day for 9 days. Survival time of treated leukemic mice is compared to that of untreated leukemic mice (T/C×100). A T/C value of 100% indicated no activity. A T/C value greater than 100% means that the treated mice are surviving longer than the control mice. A fraction giving a T/C value greater than 125% is indicative of activity as defined by the NCI Protocols, above. Activities of the fractions comprising the pure or substantially pure sesbanimide isolates as reported in Table II establish the utility of the compounds as antileukemic agents.

TABLE II
PS activity for isolated compounds

| Fraction | Compound | Host sex[1] | Dose (μg./kg./inj.)[2] | T/C[3] (%) |
|---|---|---|---|---|
| K442 | Sesbanimide B | M | 7.50 | toxic |
|  |  |  | 3.75 | 161 |
|  |  |  | 1.87 | 157 |
| K443 | Sesbanimide A | F | 32.00 | 181 |
|  |  |  | 16.00 | 149 |
|  |  |  | 8.00 | 140 |
|  |  |  | 4.00 | 119 |
|  |  |  | 2.00 | 119 |

[1]All hosts were type $CDF_1$ mice. Six replicate mice were tested at each dose level.
[2]The doses are reported as micrograms per kilogram of host body weight per injection. The injection vehicle in all cases was water.
[3]T/C = mean survival time of test animals/mean survival time of control animals; 125% or above considered active.

The utility of sesbanimide A has also been demonstrated against lymphoid leukemia L1210 in mice. This assay was conducted in accordance with the NCI Protocol 1.100 described in Geran et al., supra, page 7. Starting 24 hr. after the tumor implantation, predetermined doses of the compound were injected intraperitoneally once a day for 9 days. The results are reported in Table III as the percent T/C.

The terms "effective amount" and "effective dose" as referring to the treatment of animals are defined herein to mean these quantities of alkaloid which will promote remission of leukemia in the animal to which it is administered, without imparting a toxic response. The effective amount may vary with the injection vehicle, the injection schedule, the strain of leukemia, and other related factors, all of which may be varied without departing from the scope or operativeness of the invention. Generally an effective dose would be in the range of about 0.50–100 μg./kg. of body weight/day, and preferably in the range of about 5.0–50.0 μg./kg. of body weight/day. Any pharmaceutically acceptable vehicle or carrier may be used in conjunction with the sesbanimide.

EXAMPLE 2

Isolation of Sesbanimide—Pilot-Plant Scale. Seed material (560 kg.) was ground in a Wiley mill to pass a 3-mm. screen. The ground material (546 kg.) was placed in a 5583-l. tank with 2207 l. of methanol which was percolated over the plant material for 8 hr./day for 4 days. The extract was drained and concentrated to about one-half volume in a wiped film evaporator over a period of 2½ days. The extraction and concentration procedures were repeated three times, and in each case the extraction efficiency was determined by taking a test sample of the extract to dryness. The results were reported in Table IV, below.

TABLE III
L1210 Activity for sesbanimide A

| Compound | Host sex[1] | Dose (μg./kg./inj.)[2] | T/C[3] (%) |
|---|---|---|---|
| Sesbanimide A | F | 64.00 | toxic |
|  |  | 32.00 | 135 |
|  |  | 16.00 | 116 |

[1]All hosts were type $CDF_1$ mice. Six replicate mice were tested at each dose level.
[2]The doses are reported as micrograms per kilogram of host body weight per injection. The injection vehicle in all cases was water.
[3]T/C = mean survival time of test animals/mean survival time of control animals; 125% or above considered active.

TABLE IV

| Extraction | Methanol added (l.) | Duration (days) | Efficiency (g. solid/l.) |
|---|---|---|---|
| 1 | — | 4 | 23.1 |
| 2 | 1041 | 3 | 11.8 |
| 3 | 1249 | 3 | 6.6 |
| 4 | 1249 | 2 | 4.1 |

TLC indicated that virtually all of the sesbanimide had been removed by the end of the third extraction. The concentrate (1874 l.) from the four methanol extractions was split into nine batches, each of which was diluted with water to give a 25–30% aqueous methanol solution. The aqueous methanol extracts were partitioned three times against hexane in a hexane:aqueous MeOH ratio of about 1:6.6. The methanol:water solubles from the hexane partitions were combined into three batches of about 1874 l. each for partitioning with methylene dichloride in a solubles to $CH_2Cl_2$ volumetric ratio of about 3:1. After the mixture was vigorously stirred for 15–20 min., 3 l. of saturated NaCl solution was added to retard emulsion formation, and the mixture was allowed to separate overnight. Each extract was concentrated to about 38–57 l. by two passages through a wiped film evaporator and then in a 20-l. rotavap. A total of 11.05 kg. of crude extract comprising a thin black syrup having a solids content of 17.45% solids was collected from the three batches of $CH_2Cl_2$ soluble extracts.

Two 15 cm.×3.05 m. stainless steel columns in series were slurry packed with 62 kg. of silica gel (Davisil 633, 200–400 mesh size) in 5% MeOH in $CH_2Cl_2$, and conditioned with 151 l. of 2.5% MeOH in $CH_2Cl_2$. The concentrated syrup and a small quantity of $CH_2Cl_2$ wash solvent was pumped onto the column followed by the solvent gradient reported in Table V at the rate of 49–68 l./hr. at a pressure of 150–190 p.s.i. Fractions were collected in 19-l. containers and each was examined by TLC against a sesbanimide-containing standard. Like fractions were combined and concentrated to dryness. The column run is summarized in Table V.

Combined fractions 26–29 (42 g.) were passed through a 50-cm. "Magnum 9" HPLC column packed with "Partisil 10" at the rate of 200 mg. in 1 ml. of $CH_2Cl_2$ per injection. Eluant was 5% MeOH in $CH_2Cl_2$ at a flow rate of 6 ml./min. Like fractions from the several runs were combined and concentrated to dryness. Yields were as follows:

| Fraction | Amount (g.) |
|---|---|
| F511 | 15.5 |
| F512 | 13.4 |
| F513 | 6.6 |

| Fraction | Amount (g.) |
| --- | --- |
| F514 | 3.0 |

Fraction F512 was dissolved in 250 ml. CH$_2$Cl$_2$, and 250 ml. of ethyl ether was added. The flask containing the sample was loosely stoppered and allowed to stand until the volume was 250 ml. Upon decanting the mother liquor, crude crystalline sesbanimide (2.6 g.) was obtained and labeled as fraction F515. The ED$_{50}$ level in the KB system of F515 was $7.0 \times 10^{-3}$ μg./ml. The material was redissolved in a minimum of CH$_2$Cl$_2$ (about 100 ml.) and crystallized by slow evaporation of solvent. Five crops of pure or substantially pure sesbanimide A were recovered as reported in Table VI, below.

TABLE V

| Eluant | | | | | |
| --- | --- | --- | --- | --- | --- |
| % MeOH | % CH$_2$Cl$_2$ | Amount (l.) | Fraction | Vol. (l.) | Amount concentrate |
| 2.5 | 97.5 | 151 | 1–4 | 76 | 379 g. |
| | | | 5–7 | 57 | 25.3 |
| 5.0 | 95.0 | 221 | 8–10 | 57 | 167 |
| | | | 11–13 | 57 | 30.4 |
| | | | 14–16 | 57 | 13.2 |
| | | | 17–19 | 57 | 29.8 |
| | | | 20–21 | 38 | 31.7 |
| 10.0 | 90.0 | 220 | 22–25 | 76 | 51.5 |
| | | | 26–29 | 76 | 42.9 |
| | | | 30 | 19 | 28.1 |
| | | | 31 | 19 | 36.3 |
| | | | 32 | 19 | 35.0 |
| 50 | 50 | 151 | 33 | 19 | 22.9 |
| | | | 34–35 | 38 | 31.0 |
| | | | 36–38 | 57 | 39.4 |
| | | | 39 | 19 | 264 |
| 100 | 0 | 170 | 40–43 | 76 | 224.4 |
| | | | 44–50 | 132 | 89.4 g. |
| | | | Column drainings | | |

TABLE VI

| Crop | Amount (mg.) | Melting point (°C.) |
| --- | --- | --- |
| 1 | 356 | 159–161 |
| 2 | 160 | 161–163 |
| 3 | 412 | 161–162 |
| 4 | 389 | 162–163 |
| 5 | 345 | 158–160 |

It is understood that the foregoing detailed description is given merely by way of illustration and that modification and variations may be made therein without departing from the spirit and scope of the invention.

We claim:

1. A substantially pure chemotherapeutically active alkaloid compound sesbanimide having the following structure:

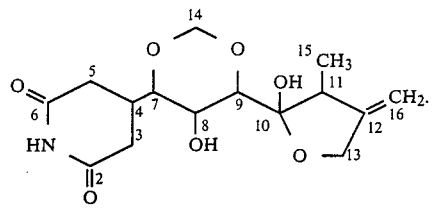

2. A substantially pure chemotherapeutically active alkaloid compound sesbanimide A as described in claim 1 and having the following relative configuration:

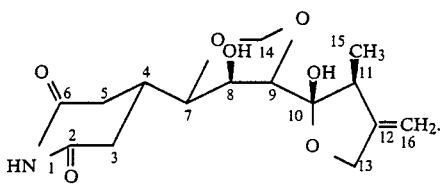

3. A substantially pure chemotherapeutically active alkaloid compound sesbanimide B as described in claim 1 and having the following relative configuration:

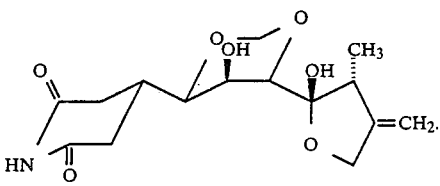

4. A chemotherapeutic composition suitable for the remission of leukemia in animals comprising a pharmaceutically acceptable vehicle and an amount of substantially pure sesbanimide effective to promote said remission.

5. The chemotherapeutic composition described in claim 4 wherein said vehicle is an injectable liquid.

* * * * *